US00PP20455P2

(12) United States Plant Patent
Larsen

(10) Patent No.: US PP20,455 P2
(45) Date of Patent: Nov. 3, 2009

(54) ***OSTEOSPERMUM* PLANT NAMED 'SUNOST0802'**

(50) Latin Name: *Osteospermum ecklonis*
Varietal Denomination: SUNOST0802

(75) Inventor: Bjarne Nyholm Larsen, Odense N. (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 12/221,680

(22) Filed: Aug. 4, 2008

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent L Bell
(74) *Attorney, Agent, or Firm*—C. A. Whealy

(57) ABSTRACT

A new and distinct cultivar of *Osteospermum* plant named 'Sunost0802', characterized by its compact and mounded plant habit; freely branching growth habit; freely flowering habit; large daisy-type inflorescences with red-colored ray florets; and good garden performance.

2 Drawing Sheets

Botanical designation: *Osteospermum ecklonis.*
Cultivar denomination: 'Sunost0802'.

BACKGROUND OF THE INVENTION

The present invention relates to a new and distinct cultivar of *Osteospermum* plant, botanically known as *Osteospermum ecklonis,* and hereinafter referred to by the name 'Sunost0802'.

The new *Osteospermum* is a product of a planned breeding program conducted by the Inventor in Odense, Denmark. The objective of the program is to create and develop new *Osteospermum* cultivars with compact and uniformly mounded plant habit, freely flowering habit and attractive inflorescence coloration.

The new *Osteospermum* originated from a cross-pollination by the Inventor in May, 2006 of *Osteospermum ecklonis* 'Sheila', disclosed in U.S. Plant Pat. No. 18,066, as the female, or seed, parent with a proprietary selection of *Osteospermum ecklonis* identified as code No. 03.70.003, not patented, as the male, or pollen, parent. The new *Osteospermum* was discovered and selected by the Inventor as a single flowering plant within the progeny of the stated cross-pollination in a controlled greenhouse environment in Odense, Denmark in May, 2006.

Asexual reproduction of the new *Osteospermum* by terminal cuttings in a controlled greenhouse environment in Odense, Denmark since November, 2007, has shown that the unique features of this new *Osteospermum* are stable and reproduced true to type in successive generations.

SUMMARY OF THE INVENTION

Plants of the new *Osteospermum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunost0802'. These characteristics in combination distinguish 'Sunost0802' as a new and distinct cultivar of *Osteospermum:*

1. Compact and mounded plant habit.
2. Freely branching growth habit.
3. Freely flowering habit.
4. Large daisy-type inflorescences with red-colored ray florets.
5. Good garden performance.

Plants of the new *Osteospermum* differ from plants of the female parent, 'Sheila', in the following characteristics:

1. Plants of the new *Osteospermum* are more freely branching than plants of 'Sheila'.
2. Plants of the new *Osteospermum* have larger leaves than plants of 'Sheila'.

Plants of the new *Osteospermum* differ from plants of the male parent selection primarily in ray floret color as plants of the male parent selection have paler red-colored ray florets. In addition, plants of the new *Osteospermum* are more upright than plants of the male parent selection.

Plants of the new *Osteospermum* can be compared to plants of the *Osteospermum* 'Sunny Fiona', disclosed in U.S. Plant patent application Ser. No. 11/821,112. In side-by-side comparisons conducted in Odense, Denmark, plants of the new *Osteospermum* differed from plants of 'Sunny Fiona' in the following characteristics:

1. Plants of the new *Osteospermum* were more freely branching than plants of 'Sunny Fiona'.
2. Plants of the new *Osteospermum* and 'Sunny Fiona' differed in ray floret color as plants of 'Sunny Fiona' have pink-colored ray florets.

BRIEF DESCRIPTION OF THE PHOTOGRAPHS

The accompanying photographs illustrate the overall appearance of the new *Osteospermum*. These photographs shows the colors as true as it is reasonably possible to obtain in colored reproductions of this type. Colors in the photographs may differ slightly from the color values cited in the detailed botanical description which accurately describe the colors of the new *Osteospermum*. The photograph on the first sheet comprises a side perspective view of a typical flowering plant of 'Sunost0802'. The photograph on the second sheet is a close-up view of a typical inflorescence of 'Sunost0802'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in Odense, Denmark during the spring in a glass-covered greenhouse and under conditions and practices which approximate those generally used in commercial *Osteospermum* production. During the production of the plants, day temperatures ranged from 14° C. to 20° C., night temperatures averaged 14° C. and light levels ranged from 200 to 800 watts per square meter. Plants were pinched one time. Plants had been growing for 15 weeks when the photographs and description were taken.

Botanical classification: *Osteospermum ecklonis* 'Sunost0802'.

Parentage:

*Female, or seed, parent.*—*Osteospermum ecklonis* 'Sheila', disclosed in U.S. Plant Pat. No. 18,066.

*Male, or pollen, parent.*—Proprietary selection of *Osteospermum ecklonis* identified as code No. 03.70.003, not patented.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; white in color.

*Rooting habit.*—Freely branching; moderately dense.

Plant description:

*Plant form/growth habit.*—Compact and mounded plant habit. Inflorescences positioned above and beyond the foliar plane. Low to moderately vigorous growth habit.

*Plant height.*—About 20 cm to 23 cm.

*Plant diameter.*—About 22 cm to 26 cm.

*Lateral branches.*—Quantity per plant: Freely branching, about five primary lateral branches per plant; pinching enhances branching. Length: About 6 cm to 9 cm. Diameter: About 5 mm. Internode length: About 1 cm. Strength: Strong. Texture: Pubescent. Color: Close to 144B.

*Foliage description.*—Arrangement: Alternate, simple. Length: About 4 cm to 6 cm. Width: About 2 cm to 4 cm. Shape: Oblanceolate to obovate. Apex: Broadly acute. Base: Attenuate to cuneate. Margin: Coarsely dentate; irregular. Texture, upper and lower surface: Smooth, glabrous; leathery; moderately dense pubescence along the leaf margins. Venation pattern: Pinnate. Color: Developing leaves, upper surface: Close to 137A. Developing leaves, lower surface: Close to 137C. Fully expanded leaves, upper surface: Close to 147A; venation, close to 146A to 146B. Fully expanded leaves, lower surface: Close to 137B; venation, close to 146B. Petiole: Length: About 2 cm. Diameter: About 2 mm to 4 mm. Texture, upper and lower surfaces: Smooth, glabrous. Color, upper surface: Close to 146C. Color, lower surface: Close to 144A.

Inflorescence description:

*Appearance.*—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright. Freely flowering habit; about 50 to 60 inflorescences develop per plant. Inflorescences not persistent. Inflorescences not fragrant.

*Flowering response.*—In northern Europe, plants of the new *Osteospermum* flower continuously from spring to late summer. Early flowering habit, plants begin flowering about eight to ten weeks after pinching. Inflorescences last about two weeks on the plant.

*Inflorescence bud.*—Height: About 1 cm. Diameter: About 1 cm. Shape: Roughly spherical. Color: Towards the base, close to 144C; towards the apex, close to 137C.

*Inflorescence size.*—Diameter: About 6.5 cm. Depth (height): About 2 cm. Disc diameter: About 5 mm to 6 mm. Receptacle diameter: About 8 mm to 10 mm. Receptacle height: About 8 mm.

*Ray florets.*—Length: About 3 cm. Width: About 8 mm. Shape: Oblanceolate. Apex: Emarginate. Base: Attenuate. Margin: Entire. Texture: Smooth, glabrous; at the base, pubescent. Number of ray florets per inflorescence: About 20 in two whorls. Color: When opening, upper surface: Close to 173B; towards the base, close to 184C. When opening, lower surface: Close to 153C; towards the base, close to 183D. Fully opened, upper surface: Towards the apex, close to 169A; mid-section, close to 179A; towards the base, close to 58A. Fully opened, lower surface: Close to 173A; stripes, close to 176A.

*Disc florets.*—Shape: Tubular; apex dentate, five-pointed. Length: About 5 mm to 7 mm. Diameter, apex: About 4 mm. Diameter, base: About 1 mm. Number of disc florets per inflorescence: About 70. Color: Immature: Apex, close to N199A; mid-section, close to 21A; base, close to 150D. Mature: Apex, close to 187B; mid-section and base, close to 155D.

*Phyllaries.*—Quantity per inflorescence: About 19 in a single whorl. Length: About 1 cm to 1.2 cm. Width: About 2 mm. Shape: Lanceolate. Apex: Acuminate, elongated. Base: Cuneate. Margin: Entire. Texture, upper and lower surfaces: Pubescent. Color, upper surface: Close to 146B. Color, lower surface: Close to 146A.

*Peduncles.*—Length, terminal peduncle: About 8 cm. Length, fourth peduncle: About 7 cm. Diameter: About 2 mm. Strength: Strong. Aspect, terminal peduncles: Mostly upright. Aspect, axillary peduncles: About 25° from vertical. Texture: Sparsely pubescent. Color: Close to 144B.

*Reproductive organs.*—Androecium: Present on disc florets only. Anther shape: Lanceolate. Anther length: About 3 mm. Anther color: Close to 163A. Pollen amount: Moderate. Pollen color: Close to 23A. Gynoecium: Present on both ray and disc florets. Pistil length: About 9 mm. Stigma shape: Lanceolate.

Stigma color: Close to N186C. Style length: About 5 mm. Style color: Close to 155D. Ovary color: Close to 145D.

*Seeds/fruits*.—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about 0° C. to about 40° C.

It is claimed:

1. A new and distinct *Osteospermum* plant named 'Sunost0802', as illustrated and described.

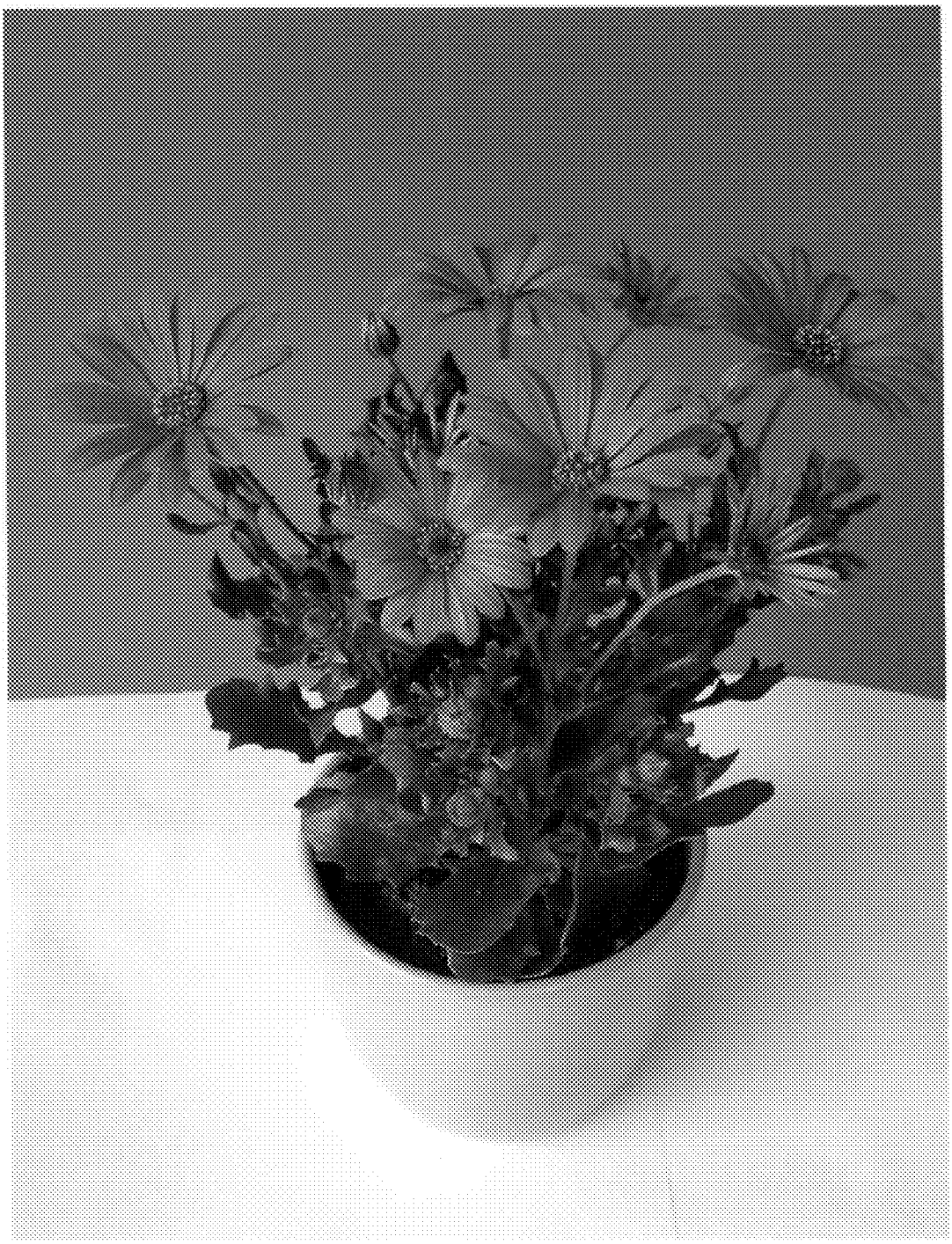

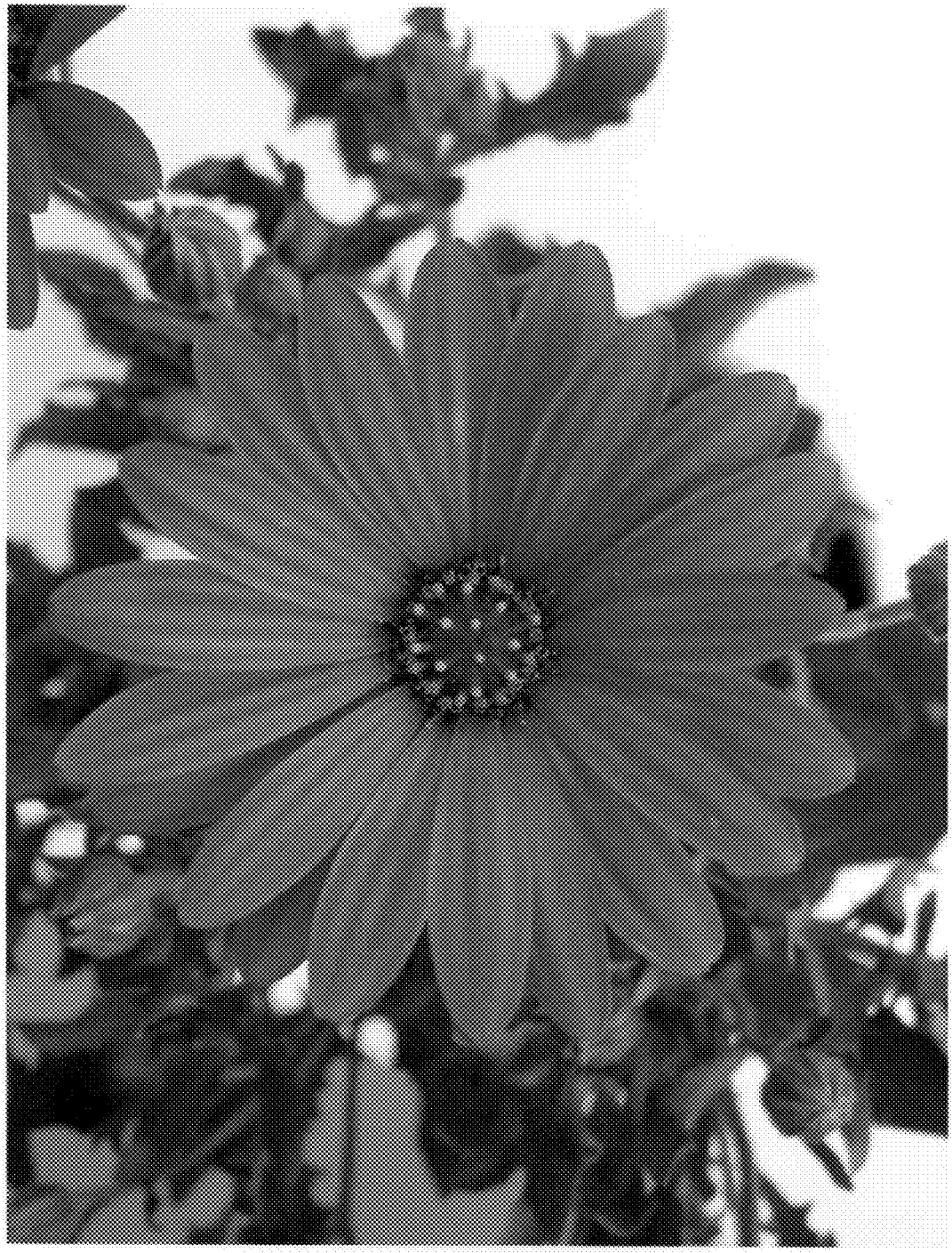

* * * * *